(12) United States Patent
McCarthy, Jr.

(10) Patent No.: US 6,997,609 B2
(45) Date of Patent: Feb. 14, 2006

(54) SYSTEM AND METHOD FOR COOLING AN X-RAY TUBE IN A TOMOGRAPHY COMPUTER SYSTEM

(75) Inventor: Joseph H. McCarthy, Jr., Dayton, OH (US)

(73) Assignee: Tark, Inc., Dayton, OH (US)

(*) Notice: Subject to any disclaimer, the term of this patent is extended or adjusted under 35 U.S.C. 154(b) by 20 days.

(21) Appl. No.: 10/315,545

(22) Filed: Dec. 10, 2002

(65) Prior Publication Data

US 2004/0109538 A1 Jun. 10, 2004

(51) Int. Cl.
*H01J 35/10* (2006.01)

(52) U.S. Cl. .................. 378/200; 378/141; 378/199

(58) Field of Classification Search ............ 378/199, 378/200, 141; 165/121, 122, 125, 169; 62/435
See application file for complete search history.

(56) References Cited

U.S. PATENT DOCUMENTS

| | | | |
|---|---|---|---|
| 3,800,866 A | 4/1974 | Ireland et al. | |
| 4,062,401 A | 12/1977 | Rudny et al. | |
| 4,115,697 A | 9/1978 | Hounsfield et al. | |
| 4,250,715 A | 2/1981 | Ratliff | |
| 4,307,778 A * | 12/1981 | Tobin et al. | 165/125 |
| 4,321,803 A * | 3/1982 | Smith | 62/507 |
| 4,739,153 A | 4/1988 | Rendel et al. | |
| 4,767,961 A | 8/1988 | Koller et al. | |
| 4,768,212 A | 8/1988 | Appelt et al. | |
| 5,172,752 A | 12/1992 | Goetz, Jr. | |
| 5,410,991 A | 5/1995 | Beaudry et al. | |
| 5,509,463 A | 4/1996 | Callaway, Sr. et al. | |
| 5,732,123 A | 3/1998 | Peralta et al. | |
| 5,956,383 A | 9/1999 | Kendall | |
| 5,970,925 A | 10/1999 | Lakerdas et al. | |
| 6,145,479 A | 11/2000 | Rotter | |
| 6,491,428 B1 * | 12/2002 | Takanashi | 378/200 |
| 2002/0118794 A1 | 8/2002 | McCarthy, Jr. | |
| 2002/0121105 A1 | 9/2002 | McCarthy et al. | |
| 2004/0240625 A1 * | 12/2004 | Kendall | 378/199 |

FOREIGN PATENT DOCUMENTS

GB 2026812 2/1980

OTHER PUBLICATIONS

"Lytron 1997 Catalog Total Thermal Solutions", pp. 12-15 and 26-29, 1997, Lytron, Inc., Woburn, MA USA.
"Product Guide," pp. 1 and 14, Feb. 1997, Comair Rotron, San Ysidro, CA USA.
Toboldt, William, "Chapter 15 Engine Cooling Systems," Automotive Encyclopedia, 1995, pp. 189-207, Goodheart Wilcox Co.

* cited by examiner

*Primary Examiner*—Allen C. Ho
(74) *Attorney, Agent, or Firm*—Jacox Meckstroth & Jenkins

(57) ABSTRACT

A system and method for cooling an X-ray tube in a computer tomography (CT) cooling system is shown having a heat exchanger that has at least one cooling passageway for receiving a coolant for cooling the X-ray tube and that is formed to define a tubular passageway having or defining a heat exchanger axis. The tubular passageway has a first open area and a second open area, and, in one embodiment a first axial fan and a second axial fan, respectively, are situated adjacent to the first and second open areas. The heat exchanger is mounted on a gantry of the computerized tomography system such that the axis of the axial fans and the heat exchanger axis are generally parallel to the gantry axis so as to reduce or minimize the effects of gyroscopic forces.

7 Claims, 4 Drawing Sheets

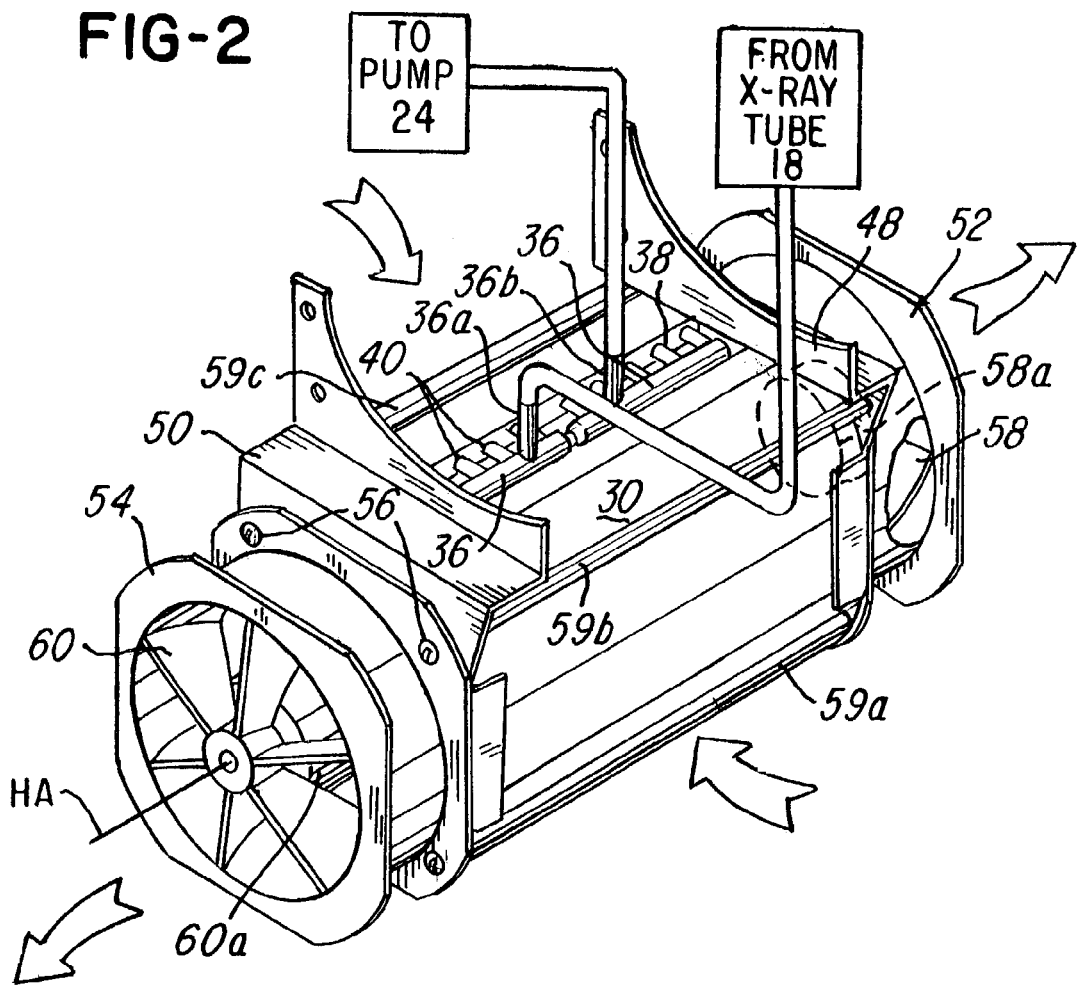
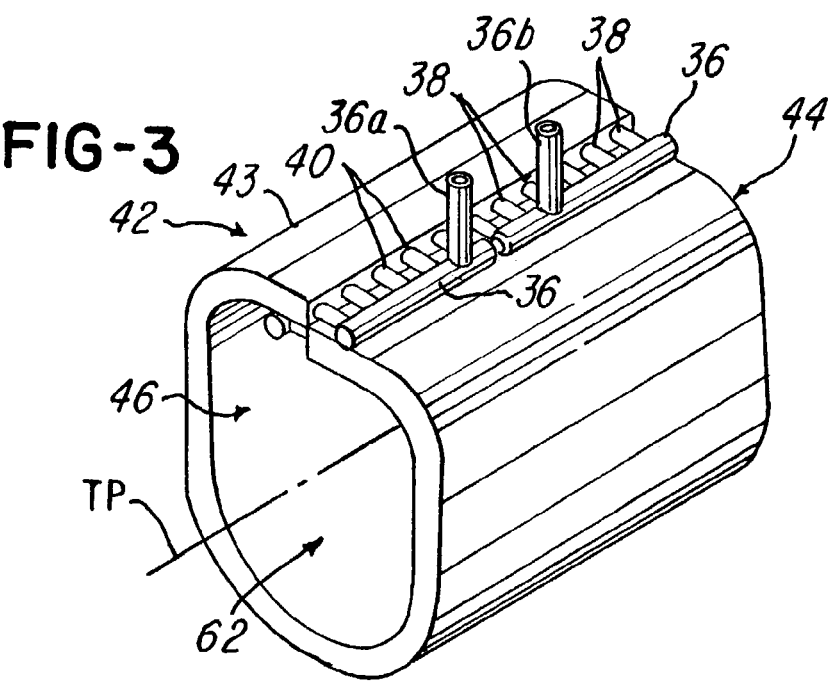

SYSTEM AND METHOD FOR COOLING AN X-RAY TUBE IN A TOMOGRAPHY COMPUTER SYSTEM

BACKGROUND OF THE INVENTION

This invention relates to an apparatus for cooling oil or other fluid or coolant which is used to carry heat away from an X-ray tube in a computed tomography (CT) diagnostic imaging system. More particularly, the invention is directed to an apparatus and method which will facilitate reducing the amount of patient time required to perform an examination using the CT diagnostic imaging system.

As is well known in the art, an X-ray tube generates substantial amounts of heat in the course of its operation. Accordingly, provision must be made for removing heat from the proximity of the tube and for dispensing the heat into the surrounding environment. In a common arrangement, a coolant fluid or oil, circulates around the tube to receive excessive heat and then flows through a conduit to a heat exchanger. In the past, the heat exchanger caused the heat stored in the oil to be exposed to the surrounding air, so that the heat can be convected thereinto. The coolant oil then flows back to the tube through a second conduit.

Cooling arrangements of the above type commonly employ a fan to move air past or through the heat exchanger, to enhance heat transfer. If the X-ray tube is used in connection with a CT system, the tube, the heat exchanger, and the cooling fan are respectively mounted on an annular gantry, which is rapidly rotated around the patient to acquire a CT image. The gantry may rotate, for example, at a minimum of 90 revolutions per minute. At present, the X-ray tube cooling fans used in CT systems tend to be axial. That is, both the intake and exhaust air streams generated by the fans are directed along the fan axis (i.e., the axis of blade rotation). To provide sufficient cooling power, axial cooling fans must be rotated at a speed on the order of 3600 revolutions per minute. The axial fans typically force the air through at least one planar radiator that was situated in the path of airflow.

Attempts have been made in the past to reduce the amount of noise and vibration caused by the axial cooling fan systems of the past. For example, U.S. Pat. No. 5,956,383 issued to Kendall discloses a radial fan arrangement for cooling an X-ray tube mounted on the gantry of a CT system. In that reference, the axis of the fan is maintained in parallel relationship with the axis of the gantry to prevent gyroscopic loading of the fan as the fan rotates about the gantry axis with the gantry.

Another problem with CT is that the cost is high. To reduce the cost per patient, there is a desire to reduce the time required to take an X-ray by increasing the operational speed of the CT system. Increasing the speed also means that the patient does not have to remain still as long to get the same image, which results in improved results. Faster processing of patients further results in higher patient throughput.

In the past, the rotational speed of the gantry of CT system increased from one revolution/second to three revolutions/second, which required more X-rays to maintain the same rate of X-rays per unit time to get the same image. This, in turn, resulted in an increase in the power requirements of the CT system, thereby requiring an increase in the cooling requirements of the cooling system in the CT system.

As the rotational speed increased, the gravitational and gyroscopic forces increase, which means that the weight of the components must be reduced while the power is increased. Therefore, the need for lighter weight radiators, fans and pumps in the CT system became important. The space available for heat exchangers in the gantry of a typical CT system is limited.

One of the problems with the prior art devices, such as the Kendall device, was that the planar radiators did not perform a cooling as quickly as desired and could not easily accommodate increases in cooling requirements.

SUMMARY OF THE INVENTION

It is, therefore, a primary object of the invention to provide a system and method for cooling an X-ray tube by providing a heat exchanger having an at least one or plurality of conduits which are formed to provide or define a passageway.

In one aspect a cooling system for a CT system is provided that utilizes a cylindrical radiator to provide a greater face area for airflow and room for more passages for liquid flow, which reduces the pressure drop across the air side and the liquid side of the radiator. This results in more airflow and more liquid flow for the same size fans and pumps. The large face area also reduces the weight of the radiator because it can be done with a thin single passage radiator instead of a smaller face area with thicker coils. This facilitates enabling the CT system to operate at higher rotational speeds, which reduces the time required to take an X-ray and also increases patient throughput.

Another object of the invention is to provide a system and method which is capable or utilizing axial fans in combination with such formed passageway.

Another object of the invention is to reduce or facilitate reducing the amount of patient time required to obtain a diagnostic image.

Still another object of the invention is to provide a system that employs an axial fan that is situated outside such a passageway defined by a radiator member formed to define such passageway.

Still another object of the invention is to provide a heat exchanger defining a passageway that is generally circular.

Still another object of the invention is to provide a heat exchanger defining a passageway that is generally rectangular.

Still another object of the invention is to provide a heat exchanger defining a passageway that is generally triangular.

Still another object of the invention is to provide a heat exchanger defining a passageway that is generally square.

In another aspect, this invention comprises a system for cooling an X-ray tube using in a radiographic device, the system comprising: a heat exchanger comprising at least one cooling passage for receiving a coolant, the heat exchanger being formed to define a tubular passageway having an axis, a first open area and a second open area, and at least one fan situated in relation to at least one of the first open area or the second open area to cause air to be forced through the heat exchanger.

In yet another aspect, this invention comprises a computerized tomography system comprising: a gantry having a gantry axis and a patient region for positioning a patient during an X-ray scanning procedure, a motor for rotatably driving the gantry, an X-ray tube mounted on the gantry, the X-ray tube having an X-ray tube axis, a heat exchanger for removing heat generated by the X-ray tube, the heat exchanger comprising at least one cooling passage for receiving a coolant and being formed to define a tubular passageway having a heat exchanger axis, a first open area and a second open area, and at least one fan situated in relation to either the first open area or the second open area to cause air to be forced through the heat exchanger to cool the X-ray tube, the at least one fan also comprising a fan axis that is substantially coaxial with the heat exchanger axis.

In still another aspect, this invention comprises a method for cooling an X-ray tube in a computerized tomography system comprising a gantry that is rotated about a gantry axis, the gantry comprising an X-ray tube mounted on the gantry, the X-ray tube having an X-ray tube axis, providing a heat exchanger for removing heat generated by the X-ray tube, the heat exchanger comprising at least one cooling passage for receiving a coolant for cooling the X-ray tube and being formed to define a tubular passageway having a heat exchanger axis, a first open area and a second open area, situating a first fan having a first axial fan axis at the first open area and a second axial fan having a second fan axis at the second open area to cause air to be forced through the heat exchanger to cool the X-ray tube, and mounting the heat exchanger on the gantry so that the gantry axis, the first fan axis and the second fan axis are generally co-axial.

Other objects and advantages of the invention will be apparent from the following description, the accompanying drawings and the appended claims.

BRIEF DESCRIPTION OF ACCOMPANYING DRAWING

FIG. 2 is a perspective view of a heat exchanger in accordance with a preferred embodiment of the invention;

FIG. 3 is a perspective view of at least one conduit formed to define a tubular passageway having or defining an axis;

DETAILED DESCRIPTION OF PREFERRED EMBODIMENT

Figure 1:
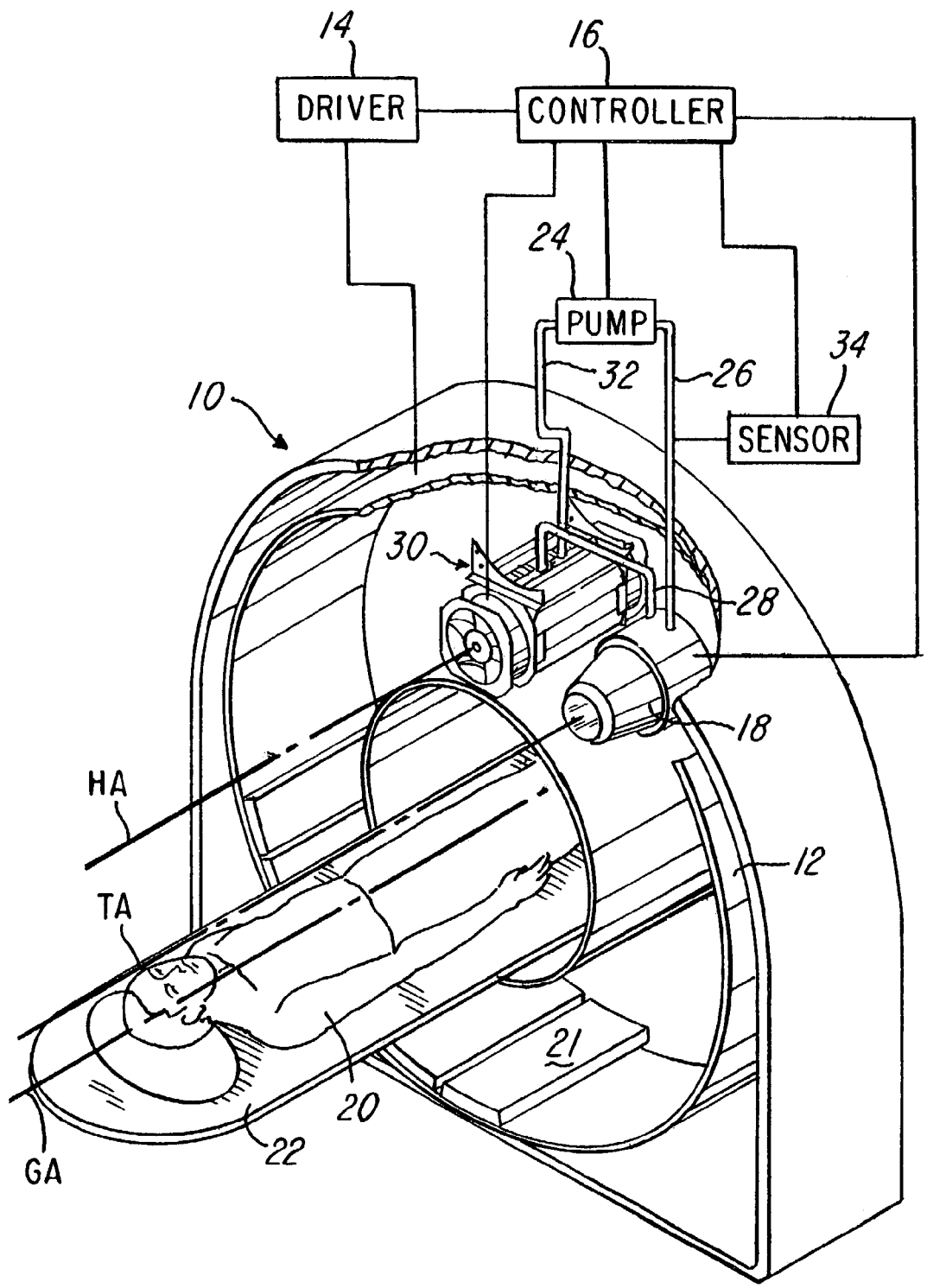
FIG. 1 is a fragmentary perspective view of a computerized tomography system in accordance with one embodiment of the invention.

Referring now to FIG. 1, a computerized tomography or radiographic device or system 10 is shown. The system 10 comprises a gantry 12 that is rotatably driven about a gantry axis GA by a drive motor 14 which is under the control of a controller 16. An X-ray tube 18 is conventionally mounted on the gantry. In a manner conventionally known, the X-ray tube 18 transmits x-radiation towards a patient 20 shown lying on table 22 as the gantry 12 is rotated about the gantry axis at a rate of, for example, about two–three revolutions per second.

In order to cool the X-ray tube 18, the system 10 further comprises a pump 24 which is coupled to controller 16 as shown. The pump 24 pumps a coolant such as oil via conduit 32 to the heat exchanger 30. The coolant is pumped from the heat exchanger 30, through conduit 28 and into an X-ray tube 18 until the coolant returns to the pump 24 via line 26. Note that the X-ray tube 18 comprises an X-ray tube axis TA and the heat exchanger 30 comprises a heat exchanger axis HA as best illustrated in FIG. 1.

It should be appreciated that the X-ray tube 18 operates within a typical predetermined temperature range, such as 30 Degrees Celsius to 80 Degrees Celsius. The system 10 further comprises a sensor 34 coupled to controller 16. If the sensor 34 senses that a temperature of the X-ray tube 18 is outside the predetermined range, then the controller 16 responds by, among other things, terminating power to the X-ray tube 18 in response to the sensed temperature. It should be appreciated, however, that the predetermined range may vary depending on the application and the type or model X-ray tube used.

Figure 4:
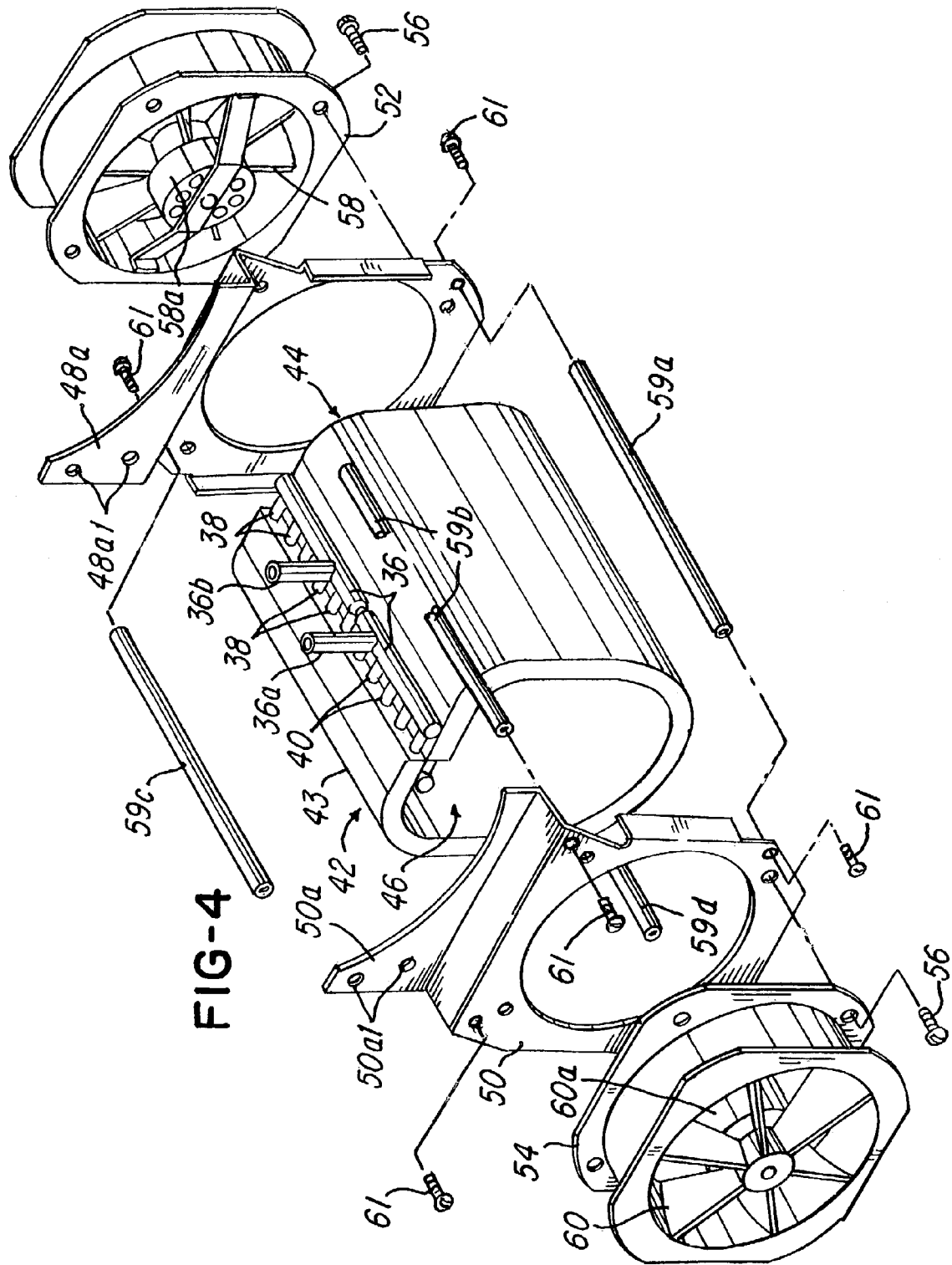
FIG. 4 is an exploded view of the heat exchangers shown in FIG. 2.

Referring now to FIGS. 2–4, the heat exchanger 30 comprises or defines at least one conduit 36 having one or more cooling passageways, such as conduits 38 and 40 which cooperate to define a radiator 42. Note that the conduits 38 and 40 comprise a material 43 which further facilitates the exchange of heat from the conduits 38 and 40 and the coolant situated therein. In the embodiment being described, the material 43 may comprise metallic fins. Note that the cooling conduit 36 comprises an inlet 36b which is coupled to the pump 24 and which receives coolant there from pump 24. The passageway 36 also comprises an outlet 36a which is coupled to the X-ray tube 18 to permit the coolant to flow through the passageway 36 tubes, such as conduits 38 and 40, where the coolant may be cooled.

As best illustrated in FIGS. 3 and 4, note that the conduit 36 and conduits 38 and 40 and material 43 are formed into a generally tubular shape to provide a generally tubular radiator 42 that defines a first open area 44 and second open area 46.

Referring back to FIG. 2, note that the heat exchanger 30 comprises a pair of mounting brackets 48 and 50 on which a pair of fan shrouds 52 and 54, respectively, are mounted by conventional means, such as a plurality of screws 56 which are received in threaded holes (not shown) in the brackets 48 and 50. Note that the first fan shroud 52 is situated adjacent to the first opening 44 (FIG. 3) so that a first axial fan 58 can be mounted in the shroud 52 in operative relationship with the first opening 44 and passageway 62. Likewise, the second fan shroud 54 receives and supports a second fan 60 in operative relationship with a second opening 46 and passageway 62. Note that the first and second fans 58 and 60 are axial fan model numbers W2E200-HH86-01 available from EBM Corporation of Farmington, Conn. In the embodiment being described, the fans 58 and 60 are provided mounted in the shrouds 52 and 54, respectively. The fans 58 and 60 are driven by motors 58a (FIG. 4) and 60a, respectively, which are controlled by controller 16 (FIG. 1). It should be appreciated that the axial fans 58 and 60 are mounted such that their axes are co-axial and define the heat exchanger axis HA mentioned earlier herein.

Thus, note that the fans 58 and 60 are situated at the first open area 44 and second open area 46, respectively. The fans 58 and 60 cooperate to force air into the tubular passageway 62 (FIG. 3) and through the tubular radiator 42 that surrounds the conduits 38 and 40.

As shown in FIG. 4, the radiator 42 is sandwiched between the mounting brackets 48 and 50 which are secured together with a plurality of rods 59a–59d. The rods 59a–59b each have threaded ends for receiving the screws 61.

FIG. 4 illustrates an exploded view of the heat exchanger 30. In the embodiment being described, the fans 58 and 60 cooperate to force air into the passageway 62 (FIG. 3); however, it should be appreciated that the fans 58 and 60 could cooperate to pull air out of the passageway 62 if desired. Also, although not shown, it should be appreciated that a single fan or series of fans could be used to provide the desired forced air. Also, the at least one of the fans 58 and 60 may be situated at positions other than outside the passageway 62, such as inside the passageway 62, if desired.

FIG. 2 illustrates the assembled view of the heat exchanger 30 shown in exploded view in FIG. 4. After the heat exchanger is assembled, the heat exchanger is mounted to the gantry 12 using the extended portions 48a and 50a of mounting brackets 48 and 50, respectively. The brackets 48 and 50 are secured to the gantry using a plurality of fasteners, such as screws, which are situated through the holes 48a1 and 50a1 and received and threaded openings (not shown) in the gantry 12.

As best illustrated in FIG. 1, note that after the heat exchanger 30 is mounted on the gantry 12, the heat exchanger 30 axis HA is generally parallel to both the X-ray tube axis TA and the gantry axis GA. It has been found that this is beneficial because of the gyroscopic forces that are in play as the gantry 12 rotates during use. It should also be appreciated that the tubular passageway defined by the radiator 42 comprises a tubular passageway axis TP (FIG. 3), and the tubular passageway TP is generally co-axial with the axes of the fans 58 and 60 and axis HA.

In the embodiment being described, the tubular passageway 62 defined by the conduits 38 and 40 may be formed to define a circular, generally rectangular, square, triangular, or any other suitable shape desired.

Figure 5:
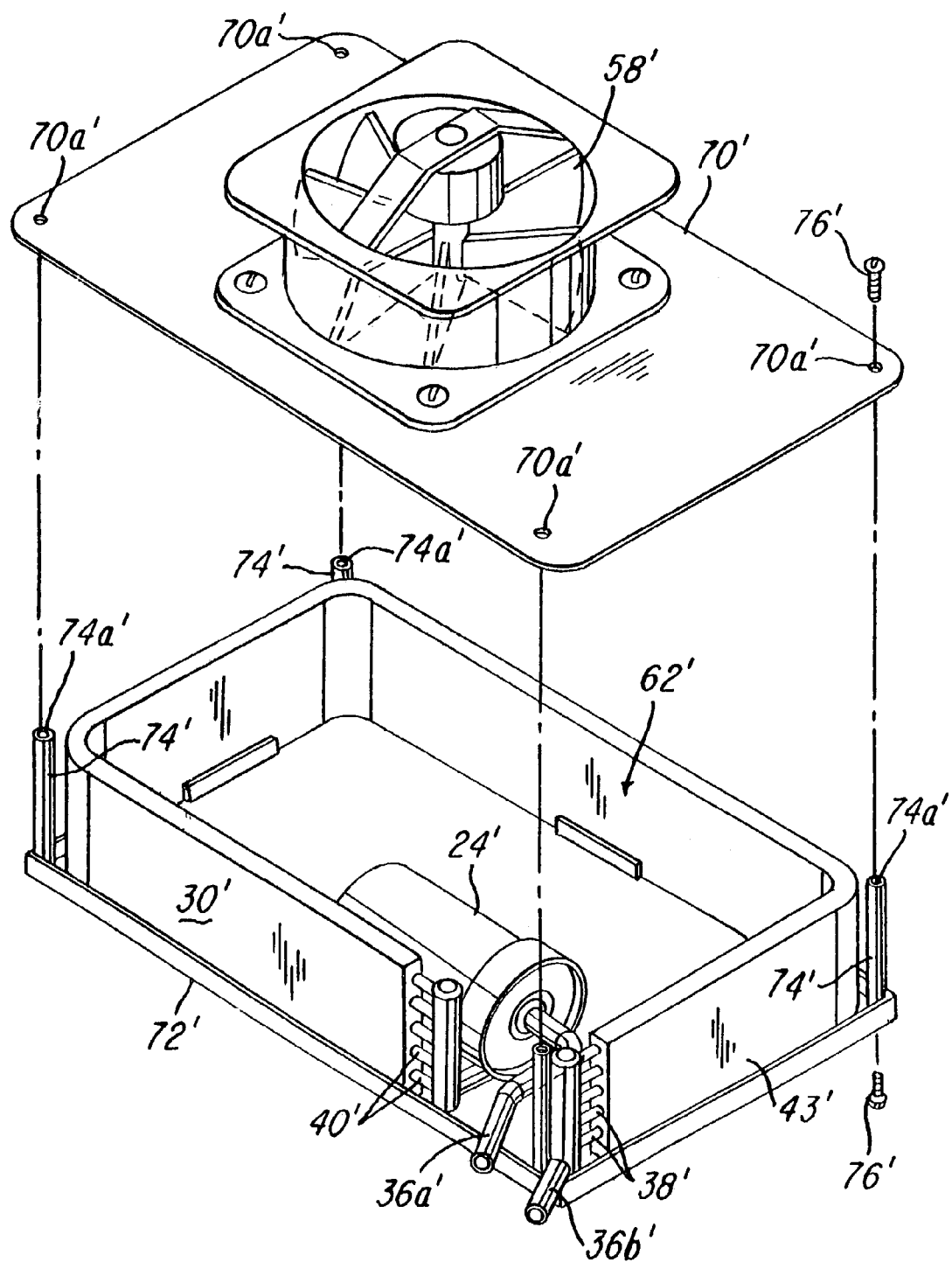
FIG. 5 is an exploded view of another embodiment of the invention.

FIG. 5 is a perspective view of another embodiment of the invention. Like parts are identified with the same part numbers, except that a prime mark ("'") has been added to the part numbers in FIG. 5. Note that the embodiment shown in FIG. 5 comprises the fluid pump 24' which is situated inside the passageway 62'. It has been found that this facilitates reducing the amount of space required by the various components, such as the heat exchanger 30' and the pump 24', when they are mounted on the gantry.

Note that the heat exchanger 30' in FIG. 5 comprises a pair of generally plainer housing members 70' and 72' that are coupled together with a plurality of support posts 74' and suitable fasteners or screws 76' which are situated in openings, such as openings 70a' and threaded into suitable openings, such as opening 70a' and member 70' and ultimately threaded into threaded openings, such as threaded opening 74a' in order to sandwich the radiator 43' between the member 70' and 72' as shown.

During operation, a technician activates controller 16 which energizes primarily to rotate gantry 12. Controller 16 energizes X-ray tube 18 to transmit radiation toward patient 20 and receivers 21 (FIG. 1). Controller 16 energizes pump 24 to pump fluid through heat exchanger 30 to cool the fluid and circulate fluid past X-ray tube 18. The technician may cause controller 16 to terminate power to the system 10 to turn it off. The controller 16 may also receive an out-of-range signal from sensor 34 in which case controller 16 terminates power to at least the X-ray tube 18 and the driver 14.

Advantageously, the system provides a system and method for cooling the X-ray tube 18 by providing the heat exchanger 30 for removing heat generated by the X-ray tube 18. As mentioned, the heat exchanger 30 comprises at least one or a plurality of coolant passageways 36 comprising at least one or a plurality of conduits 38 and 40.

While the systems and methods herein described, and the forms of apparatus for carrying these systems and methods into effect, constitute one embodiment of this invention, it is to be understood that the invention is not limited to these precise methods and forms of apparatus, and that changes may be made in either without departing from the scope of the invention, which is defined in the appended claims.

What is claimed is:

1. A method for cooling an x-ray tube in a computerized tomography system comprising the steps of:
   providing a gantry that is rotated about a gantry axis, said gantry comprising an x-ray tube mounted on the gantry, said x-ray tube having a x-ray tube axis;
   providing a heat exchanger for removing heat generated by the x-ray tube, said heat exchanger comprising at least one cooling passage for receiving a coolant for cooling said x-ray tube and being formed to define a tubular passageway having a heat exchanger axis, a first open area and a second open area;
   situating a first axial fan having a first fan axis at said first open area and a second axial fan having a second fan axis at said second open area to cause air to be forced axially through said first and second axial fans and then through said heat exchanger to cool said x-ray tube; and
   mounting the heat exchanger on said gantry so that said gantry axis, said first fan axis and said second fan axis are generally parallel.

2. The method as recited in claim 1 wherein said situating step further comprises the step of:
   situating said first and second axial fans outside said tubular passageway.

3. The method as recited in claim 2 wherein said situating step further comprises the step of:
   situating said first axial fan and said second axial fan at said first and second openings, respectively, so that the first fan axis and said second fan axis are coaxial with said heat exchanger axis.

4. The method as recited in claim 3 wherein said method further comprises the step of:
   mounting said heat exchanger on said gantry so that said heat exchanger axis is parallel to said gantry axis.

5. The method as recited in claim 1 wherein said providing step comprises the step of:
   forming said heat exchanger so that said tubular passageway defines a circular cross section.

6. The method as recited in claim 1 wherein said providing step comprises the step of:
   forming said heat exchanger so that said tubular passageway defines a rectangular cross section.

7. The method as recited in claim 1 wherein said method comprises the step of:
   situating a plurality of axial fans at either said first open area or said second open area.

* * * * *